United States Patent [19]

Prasad

[11] Patent Number: 6,090,780
[45] Date of Patent: Jul. 18, 2000

[54] HISTIDYL-PROLINE DIKETOPIPERAZINE AND METHOD OF USE

[75] Inventor: Chandan Prasad, New Orleans, La.

[73] Assignee: Chandon Prasad, New Orleans, La.

[21] Appl. No.: 09/287,452

[22] Filed: Apr. 7, 1999

[51] Int. Cl.$^7$ .................................................. A61K 38/00
[52] U.S. Cl. ............................................................ 514/11
[58] Field of Search ................................................ 514/11

[56] References Cited

U.S. PATENT DOCUMENTS

| | | |
|---|---|---|
| 4,426,378 | 1/1984 | Holaday . |
| 5,397,782 | 3/1995 | Meert . |
| 5,418,218 | 5/1995 | Wilber . |
| 5,494,898 | 2/1996 | Cheng et al. . |
| 5,500,433 | 3/1996 | Carr et al. . |
| 5,565,455 | 10/1996 | Bjork et al. . |
| 5,576,287 | 11/1996 | Zaloga et al. . |
| 5,616,311 | 4/1997 | Yen . |
| 5,618,817 | 4/1997 | Bjork et al. . |
| 5,624,910 | 4/1997 | Vallee et al. .............................. 514/27 |
| 5,643,872 | 7/1997 | Ali et al. . |
| 5,686,420 | 11/1997 | Faden . |
| 5,705,481 | 1/1998 | Jonczyk et al. . |
| 5,725,804 | 3/1998 | Yen . |

OTHER PUBLICATIONS

H. Jikihara, H. Ikegami, K. Koike, K. Wada, K. Morishige, H. Kurachi, K. Hirota, A. Miyake, and O. Tanizawa: 1993 Intraventricular Administration of Histidyl Proline Diketopiperazine [Cyclo(His–Pro)] Suppresses Prolactin Secretion and Synthesis: A Possible Role of Cyclo(His–Pro) as Dopamine Uptake Blocker in Rat Hypothalamus, Endocrinology 132: 953–958.

R. Wilcox, and B. McMillen: 1998 The Rational Use of Drugs as Therapeutic Agents for the Treatment of the Alcoholisms, Alcohol 15: 161–177.

P. Leduque, I. Jackson, A. Kervran, S. Aratan–Spire, P. Czernichow,and P. Dubois, 1987 Histidyl–Proline Diketopiperazine (His–Pro DKP) Immunoreactivity is Present in the Glucagon–containing Cells of the Human Fetal Pancreas, J. Clin. Inves. 79: 875–880.

J. Carlton, S. Khan, W. Haq, H. Mizuma, F. Ragan, B. Mathur, R. Shuklas, R. Srimal and C. Prasad: 1995 Attenuation of Alcohol–induced Hypothermia by Cyclo (His–Pro) and its Analogs, Neuropeptides 28: 351–355.

T. Stone: 1983 Actions of TRH and Cyclo (His–Pro) on Spontaneous and Evoked Activity of Cortical Neurones, Europena Journal of Pharmacology 92: 113–118.

C. Prasad, T Iruchijima, R. Rao, J. Wilber and A. Jayaraman: 1986 Distribution and Characterization of Cyclo(His–Pro)–Like Immunoreactivity in Human Cerebrospinal Fluid, Biochemical and Biophysical Research Communications 136: 835–842.

T. Yanaglsawa, C. Prasa, J. Williams and A. Peterkofsky, 1979 Antagonism of Ethanol–Induced Decrease in Rat Brain cGMP Concentration by Histidyl–Proline Diketopiperazine, A Thyrotropin Releasing Hormone Metabolite, Biochemical and Biophysical Research Communications 86: 1146–1153.

E. Reisen, J. Pearson, and C. Prasad, 1985 Failure of Cyclo (His–Pro) to Exhibit Natriuretic Activity, Neuropeptides 6: 569–572.

M. Mori, A. Jayaraman, C. Prasad, J. Pegues and J. Wilber, 1982 Distribution of histidyl–proline diketopiperazine [cyclo(His–Pro)] and thyrotrpin–releasing hormone (TRH) in the primate central nervous system, Brain Research 245: 183–186.

C. Prasad, H. Mizuma, J. Brock, J. Porter, F. Svec and C. Hilton: 1995 A Paradoxical Elevation of Brain Cyclo(His–Pro) Levels in Hyperphagic Obese Zucker Rats, Brain Research 699: 149–153.

C. Prasad: 1995 Bioactive Cyclic Dipeptides, Peptides 16: 151–164.

C. Prasad, R. Edwards, J Pegues, M. Mori, J. Wilber, R. Thomas and W. Pierson: 1984 Distribution and Characterization fo Cyclo(His–Pro)–Like Immunoreactivity in Anuran (Frog) Skins, Peptides 5: 133–136.

C. Prasad, S. Kumar, W. Atkinson and J. McGregor: 1995 Hormones in Foods: Abundance of Authentic Cyclo(His–Pro) Like Immunoreactivity in Milk and Yogurt, Nutrition Research 15: 1623–1635.

R. Wilcox and B. McMillen: 1998 The Rational Use of Drugs as Therapeutic Agents for the Treatment of the Alcoholisms, Alcohol 15: 161–177.

Y. Lamour, P. Dutar and A. Jobert: 1985 Effects of TRH, Cyclo–(His–Pro) and (3–Me–His) TRH on Identified Septohippocampal Neurons in the Rat, Brain Research 331: 343–347.

R. Lamberton, R. Lechan and M. Jackson: 1984 Ontogeny of Thyrotropin–Releasing Hormone and Histidyl Proline Diketopiperazine in the Rat Central Nervous System and Pancreas, Endocrinology 115: 2400–?.

J. Morley, A. Levine, C. Prasad: 1981 Histidyl–Proline Diketopiperazine Decreases Food Intake in Rats, Brain Research 210: 475–478.

C. Prasad and P. Balasubramanian: 1988 Cylco(His–Pro) and the Development of Tolerance to the Hypothermic Effect fo Ethanol, Neuropeptides 12: 75–79.

C. Prasad, A Jayaraman , H. Robertson and J. Rao: 1987 is All Cyclo(His–Pro) Derived from Thyrotropin–Releasing Hormone?, Nuerochemical Research 12: 767–774.

C.Prasad, T. Matsui and A. Peterkofsky: 1977 Antagonism of Ethanol Narcosis by Histidyl Proline Diketopiperazine, Nature 268: 142–144.

*Primary Examiner*—James H. Reamer
*Attorney, Agent, or Firm*—Watts, Hoffmann, Fisher & Heinke Co, L.P.A.

[57] ABSTRACT

A composition and method for attenuating the desire for alcohol in a mammal comprising administering to such mammal in need thereof, an amount effective to attenuate the desire for alcohol of a material comprising histidyl-proline diketopiperazine and a pharmaceutically acceptable carrier thereof.

21 Claims, No Drawings

HISTIDYL-PROLINE DIKETOPIPERAZINE AND METHOD OF USE

FIELD OF THE INVENTION

This invention relates to the composition and use of histidyl-proline diketopiperazine and analogues thereof for attenuating the desire for alcohol.

BACKGROUND OF THE INVENTION

Alcoholism is a major public health problem responsible for large scale morbidity and mortality and can be defined as a chronic psychiatric disorder in which a pattern of pathological alcohol use leads to serious personal and physical distress. Alcohol addiction or dependence implies a loss of control over the desire to consume ethanol. Between 80% and 90% of the population in the United States drink alcohol at some time during their lives and 30% to 40% of these may develop some temporary alcohol related problems.

Therapy in a hospital or other specialized controlled structure is the most common place for the treatment of alcohol addiction or abuse. Treatments that are used may be classified as either psychotherapy or psychopharmacology. Psychotherapies include counseling, participation in self help groups such as Alcoholics Anonymous, and the like. The generally recognized psychopharmacological treatment of ethanol withdrawal symptoms and physical changes is the administration of a mild tranquilizer such as chlordiazepoxide. Additionally, vitamins, in particular the B vitamins are administered. Optionally, magnesium sulfate and/or glucose are also administered.

While alcohol withdrawal rarely precipitates a major medical problem, alcoholic relapse after discharge of a patient from the controlled setting is very frequent. In addition to continuous psychotherapy, long term pharmacotherapies generally include an alcohol deterring agent in the treatment of alcoholics. Most of these agents have deleterious side effects that discourage continuous usage by the patient. One of the most frequently prescribed alcohol deterring agents is disulfiram. Disulfiram functions as an aldehyde dehydrogenase inhibitor. When taken with alcohol, disulfiram induces a highly unpleasant condition called the disulfiram-alcohol reaction (DAR). This highly unpleasant condition is due to the accumulation of acetaldehyde, an intermediate metabolite of alcohol. The symptoms of DAR include altered blood pressure, pulse rate, respiration rate, flushing, heat sensation, nausea, vomiting, palpitations, breathlessness and headaches. Although disulfiram is effective at making consumption of alcohol an uncomfortable experience, disulfiram does not reduce the desire for alcohol nor influence the underlying causes of the disease. This is true for many of the alcohol deterring agents prescribed. Moreover, in many cases, the symptoms from using disulfiram reach an unsafe level of circulatory changes that requires discontinuation of the treatment. As a result, patients do not feel ill enough to abstain from drinking.

While both psychotherapy and pharmacotherapy have proven to yield limited success, there still exists a need for pharmacotherapeutic agents that can attenuate the desire for alcohol with minimal or no deleterious side effects. Additionally, it is desirable for such an agent to be process selective in that it reduces alcohol dependence, but not food and water consumption. Opiates, such as morphine, naltrexone and naloxone, are believed to reduce alcohol desire by a generalized suppression of food intake and water. However, not all anorectics reduce alcohol desire. Appetite control is one of the most complex human behaviors which involves neurotransmitter systems at both the periphery and the central nervous system. This is further complicated by the chemical and pharmacological nature of the different anorectic agents that have been or are being used to control appetite. As a result, it is not possible to predict from appetite modulatory data the potential of an agent to decrease preference for alcohol.

Histidyl-proline diketopiperazine was discovered to be a major metabolite of TRH in 1976. The cyclic dipeptide, endogenous to mammals, is ubiquitously distributed throughout the central nervous system and has been shown to elicit a number of endocrine and central nervous system-related biological functions including: elevation of brain cyclic GMP concentrations; inhibition of ethanol induced sleep; decrease in food intake; hypothermia in rats; attenuation of ketamine-induced anesthesia; inhibition of dopamine uptake by rat brain striatal synaptosomes; and inhibition of prolactin secretions in vitro.

Surprisingly, applicant has discovered that histidyl-proline diketopiperazine can be useful for treating the cessation or withdrawal from the use of alcohol. In particular, histidyl-proline diketopiperazine has been found to reduce the desire for alcohol. The applicant has further discovered that the dosages required to attenuate the desire for alcohol are generally less than those dosages used for effecting appetite or water suppression.

SUMMARY OF THE INVENTION

The present invention is directed to a method for attenuating the desire for alcohol in a mammal comprising administering to such mammal in need thereof, a composition comprising histidyl-proline diketopiperazine and analogues thereof in an amount effective to attenuate the desire for alcohol. Histidyl-proline diketopiperazine and analogues thereof are easily administered, safe to use and without any of the deleterious side effects associated with alcohol deterrents, i.e. disulfiram. Moreover, the composition may be administered in combination with alcohol deterrents, such as disulfiram, at doses lower than traditionally prescribed, thereby avoiding the problems associated with taking those drugs alone.

In another embodiment, a method of attenuating the desire for alcohol comprises administering to a mammal in need thereof, an alcohol attenuating composition comprising histidyl-proline diketopiperazine in an amount wherein the appetite is not suppressed. Proper diet is generally encouraged in patients for effectively treating alcohol abuse. Advantageously, compositions comprising histidyl-proline diketopiperazine are process selective in that it can reduce dependence on alcohol, but not food and water consumption.

The inventive composition can be administered by those methods known to those skilled in the art. Methods of administration include, but are not limited to, enteral, parenteral, oral, nasal or transdermal administration. Histidyl-proline diketopiperazine and analogues thereof are comprised of amino acids and as such exhibit a low immunogenic response and are considered generally nontoxic. The composition can be safely administered in an amount ranging from about 1 µg/kg of body weight per day to about 1,000,000 µg/kg of body weight per day for reducing alcohol desire. More preferably the composition is administered orally from about 1 µg/kg of body weight per day to about 50000 µg/kg of body weight per day for reducing alcohol desire wherein appetite is not suppressed. Parenteral administration is generally 20–30% less than the oral dosage amounts as would be known to those of ordinary skill in the art in view of this disclosure.

Other objects and a fuller understanding of the invention will be had from the following description of preferred embodiments.

DETAILED DESCRIPTION

The present invention relates to a method for attenuating the desire for alcohol in a mammal by administering to such mammal in need thereof, an effective amount of histidyl-proline diketopiperazine and a pharmaceutical carrier to attenuate the desire for alcohol.

Histidyl-proline diketopiperazine, also known as cyclo (His-Pro) or CHP, is a cyclic dipeptide of histidine and proline and is derived in the mammalian body by limited proteolysis of thyrotropin releasing hormone (TRH) through the action of the brain enzyme pyroglutamyl peptidase. Alternatively, the cyclic dipeptide can be obtained by synthesis from the requisite amino acids as is known to those of ordinary skill in the art, for example, as disclosed in C. Prasad, T. Matsui, A. Peterkofsky, Antagonism of Ethanol Narcosis by Histidyl-Proline Diketopiperazine, Nature, Lond. 268: 142–144, 1977, incorporated herein by reference.

CHP is structurally unrelated to any presently used agent in the treatment of alcoholism and has been demonstrated in the present invention to attenuate the desire for alcohol in rats and mice. It will be apparent to those of ordinary skill in the art that the results obtained from these models are useful in predicting pharmacological or behavioral effects of drugs in humans. Furthermore, CHP is comprised of amino acids and as such is expected to exhibit a low immunogenic response in humans allowing a wider range of dosages. It will be further apparent to those skilled in the art that analogues of CHP will also be effective in attenuating the desire for alcohol. The term analogues includes stereoisomers of CHP as well as structurally related chemical compounds that differ slightly in composition.

While not wanting to be bound by theory, it is believed that the effect of CHP on alcohol desire is not from a generalized suppression of ingestion of food, but rather from the interaction of CHP with the serotonergic and/or dopamanergic receptors in the brain. One of the major sites for the control of appetite behavior in the brain is the hypothalmus. In contrast, the desire for alcohol is believed to be controlled by other areas in the brain such as the ventral tegmental area or nucleus accumbens.

The underlying belief that exogenous CHP administration may decrease alcohol preference results from experiments indicating that the levels of CHP in the brains of mice are directly dependent on the degree of preference for alcohol. In these experiments, eight week old male mice were obtained from Jackson Laboratories and housed individually in light controlled rooms for a period of at least twenty-one days after arrival with free access to Purina Chow and water. The lights were cycled on and off every twelve hour period. The mice included eight C57BL, six DBA/2 $F_1$-hybrid and six DBA/2 strains. C57BL strain is an inbred black mouse which exhibits a high degree of preference for alcohol in a free choice paradigm. DBA/$F_1$ strains are inbred mice which exhibit an intermediate level of preference for alcohol. DBA/2 are inbred mice which exhibit no preference for alcohol. The mice were sacrificed without anesthesia and the brains removed and processed for CHP radioimmunoassay. The radioimmunoassay involved incubating at 4–5° C. a mixture containing 0.1 ml of various dilutions of brain sample, 0.1 ml of 0.25% bovine serum albumin in phosphate buffered saline, 0.1 ml of rabbit CHP antibody and 0.1 ml of $I^{125}$-CHP. After 48 hours incubation, free and antibody bound tracers were separated by adding 1 ml of 17.5% polyethylene glycol, MW 6000 containing bovine gamma-globulin (4 mg/ml) followed by centrifugation for 20 minutes. The supernatant was discarded and the pellet was counted for radioactivity.

TABLE I

| MOUSE STRAIN | PREFERENCE FOR ALCOHOL | CHP CONCENTRATION (mean ± SEM; ng/mg protein) |
|---|---|---|
| C57BL | high | 3.01 ± 0.26 |
| DBA/$F_1$ | intermediate | 4.59 ± 0.48 |
| DBA/2 | none | 5.90 ± ~0.28 |

Results shown in Table I indicate that the levels of CHP in the brain are lower in strains that have a preference for alcohol and further support the belief that an increase in alcohol preference is due to a decrease in brain CHP content. Moreover, the data suggests that increasing CHP levels in the brain may decrease preference for alcohol.

One way to increase brain CHP levels is through exogenous administration of CHP. The cyclic dipeptide is known to resist enzymatic degradation and readily cross the blood brain barrier. Moreover, the measurement of CHP in serum has been obtained for mice and further supports the viability of exogenous CHP administration in humans. In these experiments, twenty adult male C57BL mice obtained from Jackson Laboratories were housed individually in light controlled rooms for a period of at least ten days after arrival with free access to Purina Chow and water. The lights were cycled on and off every twelve hour period. Each cage was fitted with 250 ml bottles having drip proof drinking spouts on both sides of a food bin containing Purina Chow. For the experiment, rats were divided into four groups of five mice each. Each group was treated with a different dosage of CHP dissolved in 250 milliliters of sterile water for a period of seven days. On the eighth day the mice were sacrificed and trunk blood was collected in glass test tubes. The blood was stored on ice and allowed to clot for 2 hours and centrifuged at 5° C. for 30 minutes at 2000 rpm. The serum was then collected and stored at −70° C. until processed for CHP radio-immunoassay. The radioimmunoassay involved incubating at 4–5° C. a mixture containing 0.1 ml of various dilutions of serum sample, 0.1 ml of 0.25% bovine serum albumin in phosphate buffered saline, 0.1 ml of rabbit CHP antibody and 0.1 ml of $I^{125}$-CHP. After 48 hours incubation, free and antibody bound tracers were separated by adding 1 ml of 17.5% polyethylene glycol, MW 6000 containing bovine gamma-globulin (4 mg/ml) followed by centrifugation for 20 minutes. The supernatant was discarded and the pellet was counted for radioactivity.

TABLE II

| GROUP | [CHP] IN EACH BOTTLE (µg/ml) | AVERAGE SERUM LEVEL (mean ± SEM; ng/ml) |
|---|---|---|
| I | none | 0.52 ± 0.26 |
| II | 1 | 1.14 ± 0.139 |
| III | 5 | 1.96 ± 0.43 |
| IV | 10 | 3.46 ± 0.58 |

The results shown in Table II demonstrate that exogenous administration of CHP in water significantly increased CHP serum levels (ANOVA: F=52.51, p<0.0001).

The method of treatment according to the invention involves administration of histidyl-proline diketopiperazine and a pharmaceutical carrier in therapeutically effective amounts for attenuating the desire for alcohol. Preferably, CHP is administered in an amount wherein the appetite is not suppressed. Therapeutically effective amounts, expressed in µg/kg of body weight per day, range from about 1 to about 1,000,000. More preferably CHP administration is from about 1 to about 50000 µg/kg of body weight per day. Parenteral administration generally requires lower amounts as is known to those of ordinary skill in the art. For example, when administered parenterally, CHP is preferably used in an amount of from about 1 to about 30,000 µg/kg of body weight per day. It is expected that the defined therapeutic ranges for attenuating the desire for alcohol in mice and rats will be the same or somewhat similar when the material is administered to humans.

Alternatively, CHP and analogues thereof may be administered in combination with alcoholic deterrents. Alcoholic deterrents, such as disulfiram, generally exhibit deleterious side effects that result in the patient terminating treatment. A combination of an alcoholic deterrent and CHP lowers the effective dose required for each drug. As a result, the circulatory amounts of the alcohol deterrent may not reach unsafe levels and consequently the patient may not require discontinuation of treatment.

Histidyl-proline diketopiperazine and analogues thereof may accordingly be expected to be administered to a human patient in need of such treatment corresponding to the usual routes of administration and in the usual forms. These include solutions, suspensions, emulsions, tablets, capsules and powders prepared in pharmaceutically acceptable carriers for oral administration or sterile solutions for parenteral administration.

In preparing formulations for oral administration, CHP and analogues thereof can be formulated into solid or liquid preparations such as tablets, granules, pills, powders, lozenges, sachets, cachets, elixirs, emulsions, solutions, syrups, suspensions, aerosols (as a solid or in liquid form) and soft and hard capsules. Solid unit dosage forms can be capsules of the ordinary gelatin type containing, for example, surfactants, lubricants and inert fillers such as lactose, mannitol, sucrose and cornstarch. Likewise, they can be prepared in depot, sustained release or other formulations. The depot and sustained release formulations are preferably prepared in the manner described in U.S. patent application Ser. No. 08/800,924 filed Feb. 13, 1997 and Ser. No. 09/181,204 filed Oct. 28, 1998, the disclosures of which are incorporated herein by reference in their entirety. Sustained release delivery systems include both controlled release and prolonged release. Generally, sustained release systems include any drug delivery system that achieves the slow release of drug over an extended period of time. When the system maintains constant drug levels in the blood or target tissue, it is considered a controlled release system. CHP can be tableted with conventional tablet bases such as lactose, sucrose and cornstarch in combination with binders, such as acacia, cornstarch, gelatin, disintegrating agents such as potato starch or alginic acid, and a lubricant such as stearic acid or magnesium stearate. Liquid preparations are prepared by dissolving histidyl-proline diketopiperazine in an aqueous or non aqueous pharmaceutically acceptable solvent which may also contain suspending agents, sweetening agents, flavoring agents and preservative agents as are known in the art.

For parenteral administration, histidyl-proline diketopiperazine and analogues thereof may be dissolved in a physiologically and pharmaceutically acceptable carrier and administered as either a solution or a suspension. Suitable pharmaceutically acceptable carriers are water, saline, dextrose solutions, fructose solutions or oils of animal, vegetative, or synthetic origin. The pharmaceutical carrier may also contain preservatives, buffers, etc. as is known in the art.

The following examples are detailed description of methods of preparation and use of the composition of the present invention for attenuating the desire for alcohol. The detailed preparations fall within the scope of, and serve to exemplify, the more generally described methods set forth above. The examples are presented for illustrative purposes only, and are not intended to limit the scope of the invention.

EXAMPLE 1

Preparation of CHP

Synthetic benzyloxycarbonyl-L-histidyl-L-prolineamide was prepared by coupling benzyloxcarbonyl-L-histidine (20 mmol, ICN) with L-prolineamide (20 mmol, Aldrich Chemicals), N-ethylmorpholine (20 mmol, Aldrich Chemicals) and dicyclohexylcarbodiimide (20 mmol, Pierce Chemicals). The solution in 175 mls of dimethylformamide was stirred in an ice bath for 3 hours and then overnight at room temperature. After removal of the precipitated dicyclohexylurea, the solution was evaporated to dryness in vacuo, then dissolved in approximately 25 mls of water. The solution was applied to a column (3×20 cm) of diethylaminoethylcellulose (Whatman DE-23, free base). The column was eluted with water and 10 ml size fractions were collected. Each fraction was tested for Pauly positive material. Those fractions that were Pauly positive were pooled and concentrated to dryness in vacuo. The reaction product was crystallized 4 times from hot water to yield 500 mg. Elemental analysis showed C, H, N, and O at 58.94%, 6.04%, 18.04% and 16.90%, respectively. (Microanalysis, Inc., Wilmington, Del.). Theoretical calculated values for C, H, N and O are 59.21%, 6.02%, 18.17% and 16.60% respectively.

Benzyloxycarbonyl-L-histidyl-L-prolineamide (500 mg) was dissolved in a solution containing methanol (10 ml), H2O (0.3 ml) and glacial acetic acid (0.3 ml). After adding palladium black catalyst (100 mg), the suspension was hydrogenated under 40 pounds of pressure for 2 hours. The catalyst was then filtered and the resultant solution was heated in boiling water for 30 minutes, then dried in vacuo. After dissolving the product in water, it was purified by passage through a column (2×5 cm) of diethylaminoethylcellulose and subsequently washed with water. The Pauly positive fractions were concentrated to dryness in vacuo to yield crystalline L-histidyl-L-proline diketopiperazine (yield approximately 200 mg). Elemental analysis showed C, H, N, and O at 54.75%, 6.08%, 22.10% and 17.22% respectively. Theoretical calculated values for C, H, N and O are 53.91%, 6.25%, 22.86% and 16.97% respectively. Mass spectrographic analysis showed prominent ions at m/e 234, m/e 154, m/e 81 and m/e 70. Proton NMR showed chemical shifts at 1.95, 2.2, 3.4, 3.5, 4.65, 7.4, 8.25 ppm downfield from trimethylsilane. Amino acid analysis showed the presence of ninhydrin-positive material corresponding to only proline and histidine with a ratio of 1.1 to 1.

EXAMPLE 2

Effect of CHP Administration on Voluntary Alcohol Consumption in Alcohol Naive Mice Forty adult male C57BL mice were obtained from Jackson Laboratories and housed individually in light controlled rooms for a period of at least ten days after arrival with free access to Purina Chow and water. The lights were cycled on and off every twelve hour period. Mice were divided into four groups of ten. Each room was fitted with two 250 ml bottles having drip proof drinking spouts on both sides of a food bin containing Purina Chow. One bottle contained 6% (V/V) ethanol in water whereas the other bottle contained water. Increasing concentrations of CHP were added to each bottle and distributed according to group. The two bottles were frequently exchanged with each other to minimize positional preference. Fluid intake from each bottle was recorded after 7 days.

TABLE III

| GROUP | [CHP] IN EACH BOTTLE | % ETHANOL PREFERENCE (mean ± SEM) | AVERAGE FLUID INTAKE (ml/day) |
|---|---|---|---|
| I | none | 52 ± 8 | 2.7 |
| II | 1 µg/ml fluid | 29 ± 6 | 2.9 |
| III | 5 µg/ml fluid | 23 ± 6 | 2.8 |
| IV | 10 µg/ml fluid | 15 | 2.7 |

Ethanol preference was calculated as ethanol intake/(ethanol intake+water intake)×100. The data shows a dose dependence decrease in alcohol preference after CHP administration (ANOVA: F=3.73, p=0.019). The group receiving the highest amounts of CHP showed the lowest ethanol preference. The decrease in alcohol preference is not due to a general decrease in drinking since CHP did not effect average daily fluid intake (ANOVA: F=0.09, p=0.96). Thus, the group receiving the highest amounts of CHP had comparable fluid intakes as the other groups receiving lower amounts of or no CHP.

EXAMPLE 3

Effect of CHP Administration on Voluntary Alcohol Consumption in Alcohol Experienced Mice Forty adult male C57BL mice were obtained from Jackson Laboratories and housed individually in light controlled rooms for a period of at least ten days prior to beginning the experiment with free access to Purina Chow and water. The lights were cycled on and off every twelve hour period. The mice were divided into four groups of ten. Each room was fitted with two 250 ml bottles having drip proof drinking spouts on both sides of a food bin containing Purina Chow. Both bottles contained 6% (V/V) ethanol in water and were the only source of fluid available. Mice were allowed to drink for seven days. On the eighth day, one bottle containing ethanol in water was removed and replaced with a 250 ml bottle containing water. Increasing concentrations of CHP were added to each bottle and distributed according to group. The bottles were frequently exchanged to discourage positional preference. Fluid intake from each bottle was recorded after an additional 7 days. % Ethanol preference was calculated for each group.

TABLE IV

| GROUP | [CHP] IN EACH BOTTLE | ETHANOL PREFERENCE (%) |
|---|---|---|
| I | none | 78 |
| II | 1 µg/ml fluid | 58 |

TABLE IV-continued

| GROUP | [CHP] IN EACH BOTTLE | ETHANOL PREFERENCE (%) |
|---|---|---|
| III | 5 µg/ml fluid | 54 |
| IV | 10 µg/ml fluid | 40 |

The data clearly shows a dose dependence decrease in alcohol preference after CHP administration (ANOVA: F=3.88, p=0.0195) by the alcohol experienced mice. Group IV, the alcohol experienced mice receiving the highest amount of CHP, showed the lowest ethanol preference.

EXAMPLE 4

Effect of Intraperitoneal and Oral Administration of CHP on Food Intake

Thirty-six outbred adult male Sprague-Dawley rats, certified virus free, obtained from Hilltop Laboratories, New York, N.Y. were housed in a temperature and light controlled room for a period of at least seven days after arrival. Sprague-Dawley rats are white albino outbred rats. The temperature of the room was maintained at about 20–21° C. The lights in the room were cycled between on and off every twelve hours. The rats were allowed free access to Purina Chow food and water prior to beginning the experiment. For the experiment rats were divided into six groups of six rats each. Each group was treated with a different dosage of CHP dissolved in 0.5 milliliters of sterile water. The amount of CHP in each dose was based on the body weight of the individual rat. Rats were fasted for about 21 hours from food but not water. Oral dosages of CHP were administered using a gavage tube according to each rat group. The rats were then given access to Purina Chow and water for the next seven hours. Food intake during the seven hours was measured in grams per rat and averaged for each group. The rats were then allowed to rest for 10 days to eliminate from the body any residual CHP. At the end of this period, the experiment was repeated using intraperitoneal administration.

TABLE V

| GROUP | CHP DOSAGE (mg/kg of body weight) | ORAL ADMINISTRATION (food intake g/rat, mean ± SEM, n = 6) | INTRAPERITONEAL ADMINISTRATION (food intake g/rat, mean ± SEM, n = 6) |
|---|---|---|---|
| I | 0 | 14.7 ± 2.2 | 14.3 ± 3.1 |
| II | 1 | 14.3 ± 2.2 | 17.6 ± 3.6 |
| III | 5 | 14.7 ± 1.2 | 14.2 ± 0.7 |
| IV | 10 | 13.1 ± 2.1 | 14.1 ± 2.9 |
| V | 20 | 15.1 ± 2.3 | 14.4 ± 1.0 |
| VI | 50 | 15.7 ± 1.7 | 14.7 ± 1.2 |

Statistical analysis of the data showed that oral (ANOVA; F=0.92, p0.48, n=6) or intraperitoneal (ANOVA, F=1.86, p=0.13, n=6) administration of CHP up to 50 mg/Kg of body weight had no significant effect on food consumption. Thus, all groups showed a similar appetite regardless of the amount of CHP administered.

Thus, in view of the foregoing, a preferred embodiment is a method for attenuating the desire for alcohol in a mammal by administering an effective amount of histidyl-proline diketopiperazine and a pharmaceutical carrier. The experimental results clearly demonstrate that histidyl-proline diketopiperazine is useful for reducing the desire for alcohol. Moreover, exogenous administration is process selective in that it reduces desire for alcohol, but not food and water consumption.

Although the invention has been described in its preferred form with a certain degree of particularity, it is understood that the present disclosure of the preferred form has been made only by way of example and that numerous changes in the details of construction, operation and the combination and arrangement of parts may be resorted to without departing from the spirit and the scope of the invention as hereinafter claimed.

What is claimed is:

1. A method for attenuating the desire for alcohol in a mammal comprising administering to a mammal in need thereof, histidyl-proline diketopiperazine or a stereoisomer or combinations thereof in an amount effective to attenuate the desire for alcohol.

2. The method of claim 1 wherein said material is administered enterally.

3. The method of claim 1 wherein said material is administered parenterally.

4. The method of claim 1 wherein said material is administered transdermally.

5. The method of claim 1 wherein said material is administered nasally.

6. The method of claim 1 wherein said material is administered orally.

7. The method of claim 1 wherein said histidyl-proline diketopiperazine or a stereoisomer or combinations thereof are administered in an amount ranging from about 1 $\mu$g/kg of body weight per day to about 1,000,000 $\mu$g/kg of body weight per day.

8. The method of claim 1 wherein said histidyl-proline diketopiperazine or a stereoisomer or combinations thereof are administered in an amount ranging from about 1 $\mu$g/kg of body weight per day to about 50,000 $\mu$g/kg of body weight per day.

9. The method of claim 1 wherein said histidyl-proline diketopiperazine or a stereoisomer or combinations thereof are administered in the form of a composition comprising an aldehyde dehydrogenase inhibitor and a pharmaceutically acceptable carrier.

10. The method of claim 9 wherein said aldehyde dehydrogenase inhibitor is disulfiram.

11. The method of claim 1 wherein said mammal is a human.

12. A method of attenuating the desire for alcohol comprising administering to a mammal in need thereof, an alcohol attenuating composition comprising histidyl-proline diketopiperazine or a stereoisomer or combinations thereof in an amount wherein appetite is not suppressed.

13. The method of claim 12 wherein said composition is administered enterally.

14. The method of claim 12 wherein said composition is administered parenterally.

15. The method of claim 12 wherein said composition is administered transdermally.

16. The method of claim 12 wherein said composition is administered orally.

17. The method of claim 12 wherein said histidyl-proline diketopiperazine or a stereoisomer or combinations thereof are administered in an amount ranging from about 1 $\mu$g/kg of body weight per day to about 50,000 $\mu$g/kg of body weight per day.

18. The method of claim 12 wherein said composition further comprises an aldehyde dehydrogenase.

19. The method of claim 18 wherein said aldehyde dehydrogenase is disulfiram.

20. The method of claim 12 wherein said mammal is a human.

21. A composition comprising histidyl-proline diketopiperazine or a stereoisomer or combinations thereof in an amount effective to attenuate a desire for alcohol but which does not suppress appetite and a pharmaceutical acceptable carrier.

* * * * *

UNITED STATES PATENT AND TRADEMARK OFFICE
CERTIFICATE OF CORRECTION

PATENT NO.: 6,090,780
DATED: July 18, 2000
INVENTOR(S): Chandan Prasad

It is certified that an error appears in the above-identified patent and that said Letters Patent is hereby corrected as shown below:

The following should be deleted from the face of the patent.

[73] Assignee: Chandon Prasad, New Orleans, La.

Signed and Sealed this

First Day of May, 2001

*Attest:*

NICHOLAS P. GODICI

*Attesting Officer*      *Acting Director of the United States Patent and Trademark Office*